United States Patent [19]

Edwards

[11] Patent Number: 5,059,719

[45] Date of Patent: * Oct. 22, 1991

[54] ALKOXYLATION PROCESS USING CATALYST OF THE LANTHANUM SERIES

[75] Inventor: Charles L. Edwards, Houston, Tex.

[73] Assignee: Shell Oil Company, Houston, Tex.

[ * ] Notice: The portion of the term of this patent subsequent to Oct. 15, 2008 has been disclaimed.

[21] Appl. No.: 498,483

[22] Filed: Mar. 23, 1990

Related U.S. Application Data

[63] Continuation of Ser. No. 134,272, Dec. 17, 1987, abandoned.

[51] Int. Cl.$^5$ .............................................. G07C 41/03
[52] U.S. Cl. .................................... 568/618; 568/608; 568/620; 568/45; 568/55; 568/678; 568/679; 260/410.6; 560/43; 560/209; 560/250; 560/105; 560/112; 560/240; 564/399; 564/475; 564/505; 530/217; 530/230; 530/232
[58] Field of Search ................. 568/618, 620, 608, 45, 568/55, 678, 679; 260/410.6; 560/93, 209, 200, 105, 112, 240; 564/399, 475, 505; 530/217, 230, 232

[56] References Cited

U.S. PATENT DOCUMENTS 3,328,467  6/1967  Hamilton ............................ 568/618
4,528,364  7/1985  Prier .
4,658,065  4/1987  Aoshima et al. .

FOREIGN PATENT DOCUMENTS 180266  5/1986  European Pat. Off. ............ 568/618
180267  5/1986  European Pat. Off. ............ 568/618

*Primary Examiner*—Howard T. Mars
*Attorney, Agent, or Firm*—Pamela J. McCollough

[57] ABSTRACT

Alkylene oxide adducts of organic compounds having active hydrogen atoms are prepared by a process which comprises contacting and reacting an alkylene oxide reactant comprising one or more $C_2$ to $C_4$ vicinal alkylene oxides with an active hydrogen containing reactant comprising one or more compounds having active hydrogen atoms in the presence of a catalytically effective amount of one or more soluble basic compounds of one or more elements of the lanthanum series (atomic numbers 57-71, inclusive). The product alkoxylates are known to be useful, for instance, as nonionic surfactants, wetting and emulsifying agents, solvents, and chemical intermediates. When the process is applied to the preparation of alkylene oxide, particularly ethylene oxide, adducts of alkanols, particularly primary alkanols in the $C_6$ to $C_{24}$ range, the product is a valuable narrow range nonionic surfactant, characterized by relatively narrow distribution of alkylene oxide adducts.

30 Claims, No Drawings

ALKOXYLATION PROCESS USING CATALYST OF THE LANTHANUM SERIES

This is a continuation of application Ser. No. 07/134,272, filed Dec. 17, 1987, now abandoned.

BACKGROUND OF THE INVENTION

This invention relates to an alkoxylation process in which alkylene oxides are reacted with compounds having active hydrogen atoms in the presence of catalysts comprising one or more soluble basic compounds of elements of the lanthanum series. In particularly preferred embodiments, the invention relates to the preparation of nonionic alkanol alkoxylates useful as surfactants by alkoxylation of detergent-range, i.e., $C_8$ to $C_{20}$, alkanols.

A large variety of products useful, for instance, as nonionic surfactants, wetting and emulsifying agents, solvents, and chemical intermediates, are prepared by the addition reaction (alkoxylation reaction) of $C_2$ to $C_4$ alkylene oxides with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home.

An illustration of the preparation of an alkanol ethoxylate (represented by formula III below) by addition of a number (n) of ethylene oxide molecules (formula II) to a single alkanol molecule (formula I) is presented by the equation

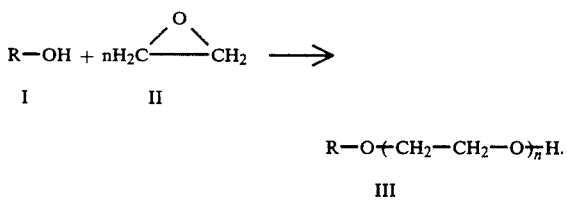

$$R-O+CH_2-CH_2-O+_nH.$$

III

The addition of alkylene oxides to alcohols and other active-hydrogen containing compounds is known to be desirably promoted by a catalyst, most conventionally a catalyst of either acidic or basic character. Recognized in the art as suitable basic catalysts are the basic salts of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, the Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids; perchloric acid and the perchlorates of magnesium, calcium, manganese, nickel and zinc., metal oxalates, sulfates, phosphates, carboxylates and acetates, alkali metal fluoroborates; zinc titanate; and metal salts of benzene sulfonic acid.

In one important aspect, the present invention relates to an alkoxylation process for the preparation of a product characterized by a narrow range (or peaked) alkylene oxide adduct distribution. Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service.

In certain preferred embodiments, the present invention provides a process characterized by enhanced selectivity for the preparation of alkoxylate mixtures in which a relatively large proportion of the alkoxylate molecules have a number (n) of alkylene oxide adducts that is within a relatively narrow range of values. It has been reported that alcohol alkoxylate products having such a narrow range distribution are preferred for use in certain detergent formulations (Great Britain Patent No. 1,462,134; Derwent Publications Research Disclosure number 194,010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Patent No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantage in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids.

Also of substantial importance in the alkoxylation of active hydrogen reactants is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often of disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. Nos. 4,306,093 and 4,239,917, and published European Patent Applications 0026544, 0026546, 0026547 and that certain compounds of barium, strontium, and calcium promote narrow-range alkoxylation products. U.S. Pat. Nos. 4,210,764 and 4,223,164 describe the use of cresylic acids to promote alkoxylation catalyzed by barium and strontium compounds. U.S. Pat. No. 4,302,613 reports that a more peaked reaction product can be obtained by combining barium and strontium alkoxylation catalysts with cocatalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorous, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorous acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorite.

U.S. Pat. Nos. 4,665,236 and 4,689,435 describe a process for the alkoxylation of active hydrogen reactants using certain bimetallic oxo catalysts. The catalysts described in U.S. Pat. No. 4,665,236 include certain neutral (rather than basic) lanthanum compounds.

SUMMARY OF THE INVENTION

It has now been found that soluble basic compounds of elements of the lanthanum series are effective catalysts for the addition reaction of alkylene oxides with organic compounds having active hydrogen atoms.

Accordingly, in the broad sense, the invention is a process for the preparation of alkoxylates of active hydrogen containing organic compounds, which comprises contacting an alkylene oxide reactant comprising one or more lower (e.g., $C_2$ to $C_4$) vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalytically effective amount of one or more soluble basic compounds of one or more of the elements of the lanthanum series.

In particularly preferred embodiments, the alkylene oxide reactant is ethylene oxide and the active hydrogen reactant contains one or more $C_6$ to $C_{30}$ alkanols. The alkanol ethoxylate resulting from this process, characterized by a narrow-range distribution of ethylene oxide adducts and a low residual alkanol content, is a valuable detergent product.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more lower vicinal alkylene oxides, particularly those in the $C_2$ to $C_4$ range. Reactants which comprise ethylene oxide, propylene oxide, or mixtures of ethylene oxide and propylene oxide are more preferred, while reactants wherein the alkylene oxide content consists essentially of ethylene oxide are considered particularly preferred.

Likewise, the active hydrogen reactants suitably utilized in the process of the invention include those known in the art for reaction with alkylene oxides and conversion to alkoxylate products. The suitable classes of active hydrogen reactants include (but are not necessarily limited to) alcohols, phenols, thiols (mercaptans), amines, polyols, carboxylic acids, and mixtures thereof. Preferably, the active hydrogen containing reactant consists essentially of one or more active hydrogen containing compounds selected from the group consisting of alcohols, phenols (including substituted phenols) and polyols.

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols and phenols are today the principal reactants in commercial alkoxylate production and are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, p-decylphenol, didecyl phenol and the like.

Acyclic aliphatic alcohols (or alkanols) form a most preferred class of reactants. In this regard, it is found that the alkanols benefit to a relatively great degree from the capabilities of the invention for the preparation of alkoxylates having narrow-range or peaked alkylene oxide adduct distributions. This is particularly true for the primary mono-hydric alkanols, although secondary and tertiary alkanols as well as polyhydric alkanols are also very suitably utilized in the process of the invention. Preference can also be expressed, for reason of both process performance and commercial value of the product, for aliphatic alcohols having from one to about 30 carbon atoms, with $C_6$ to $C_{24}$ alcohols considered more preferred and $C_8$ to $C_{20}$ alcohols considered most preferred. As a general rule, the alkanols may be of branched or straight chain structure, although preference further exists for alkanol reactants in which greater than about 50 percent, more preferably greater than about 60 percent and most preferably greater than about 70 percent of the molecules are of linear (straight-chain) carbon structure.

The general suitability of such alkanols as reactants in alkoxylation reactions is well recognized in the art. Examples of specific alkanols and of commercially available alkanols and alkanol mixtures within this class are also well known and are recited in the aforementioned U.S. Patents and published patent applications, the relevant disclosures of which exemplifying such specific alkanols and alkanol mixtures as alkoxylation process reactants are incorporated herein by this reference. Commercially available mixtures of primary mono-hydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91), mixtures of $C_{12}$ and $C_{13}$ alkanols (NEODOL 23), mixtures of $C_{12}$, $C_{13}$, $C_{14}$, and $C_{15}$ alkanols (NEODOL 25), and mixtures of $C_{14}$ and $C_{15}$ alkanols (NEODOL 45); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418), and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

For purposes of the invention, the alkylene oxide reactant and the active hydrogen reactant are necessarily contacted in the presence of a catalyst comprising one or more soluble basic compounds of one or more of the elements of the lanthanum series, that is, elements of atomic number 57 through 71, inclusive (i.e., lanthanum as well as cerium, praseodymium, neodymium, promethium, samarium, europium, gadolinium, terbium, dysprosium, holmium, erbium, thulium, ytterbium, and lutetium).

The catalyst is described as soluble in the sense that basic compounds are soluble in catalytically effective amount in the liquid active hydrogen reactant and, as the reaction proceeds, in a mixture of the active hydrogen reactant and the alkoxylate product. It is suitable to practice the invention using catalyst compounds which have limited solubility in the reaction mixture, so long as these compounds are soluble to the extent that they will have catalytic effect. In such cases, quantities of added lanthanum series compounds in excess of solubility limits suitably remain in a slurry in the mixture.

The catalyst is described as basic in the conventional sense, indicating that a hydrolyzed sample of an alkoxylation reaction mixture containing compound(s) of the lanthanum series in a catalytically effective amount (e.g., a 1 percent by weight (% w) mixture of the reaction mixture in water) has a pH greater than 7.0. In preferred embodiments of the invention, the pH of such a hydrolyzed sample is typically greater than 8.0. While the alkoxylation reaction proceeds, the reaction mixture containing the catalyst necessarily remains of alkaline pH.

The catalyst in a given application of this process suitably contains compounds of either one or a mixture of the lanthanum series elements. The natural mineral ores which serve as the commercial sources of the elements of the lanthanum series generally contain several, and in many cases all, of the elements in the series. These ores are often refined without separating the mixture into distinct elements. For this reason, the use in the invention of compounds of mixtures of the lanthanum series elements may be preferred from the standpoint of availability and cost. One example of a suitable class of such mixtures of lanthanum series elements is that known as didymium.

In addition to a catalytically effective amount of the soluble basic compounds of the lanthanum series, the catalyst for the process of the invention may also suitably contain other substances, including both those which may be introduced into the process as impurities in the lanthanum series compounds as well as those which may be added to promote or modify catalyst activity.

Either in the case of the use as catalyst of one or more compounds of a single lanthanum series element or in the case of the use of mixtures of compounds of different elements, preference can be expressed for catalysts which comprise catalytically effective amount(s) of one or more soluble basic compounds of one or more of the members of the group consisting of lanthanum, cerium, neodymium, and praseodymium. Cerium compounds form a preferred class for use in the invention. Compounds of the element lanthanum are particularly preferred.

A lanthanum series compound suitable for use in the invention is suitably either a soluble, basic compound per se or a precursor which is converted to a soluble, basic compound upon interaction with the alkoxylation process reactants (and/or products). Specific examples of compounds which are both basic per se and soluble in one or more of the suitable active hydrogen containing reactants include the alcoholate, ammoniate, amide, and nitride compounds. Representative of suitable catalyst precursors which are not basic per se but which are converted into soluble, basic compounds in the presence of alkoxylation process reactants (and/or products) are the phenolate, thiolate, thiophenoxide, and carboxylate compounds.

Preferred for use as catalyst compounds are the alcoholates and phenolates (and most preferably the alkoxides), particularly where the active hydrogen containing reactant consists essentially of an alcohol (or, in preferred embodiments, an alkanol). It will be understood that such compounds can take several forms. Thus, for instance, in the case of a catalyst compound which is an alcoholate or phenolate of the element lanthanum (La III), the preferred catalyst compounds have the formula

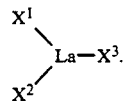

(Catalyst compounds of other lanthanum series elements can be similarly represented with the number of X substituents reflecting in each case the element's valence state.) At least one of the X substituents in such a formula then represents an alcoholate or phenolate —OR moiety. For the preferred alkoxide and phenoxide compounds, the R group in the —OR moiety is selected from the group consisting of alkyl and (optionally alkyl-substituted) phenyl moieties, more preferably $C_1$ to $C_{30}$ alkyl and optionally alkyl-substituted phenyl moieties. The X substituent(s) which represent —OR groups suitably represent the same or different —OR groups. Since the invention contemplates the possibility of the use of precursor compounds, any or all of the X groups can also represents a precursor moiety which undergoes conversion to an —OR moiety in the process mixture, and particularly in the presence of the active hydrogen containing reactant. The one or more of the X substituents which are not either —OR groups or precursors for the formation of —OR groups suitably represent other organic or inorganic moieties which do not adversely interfere with the desired catalytic activity for the alkoxylation. Very suitably, all of the X groups represent (or are in practice converted to) the same or different —OR groups.

Specific examples of preferred alkoxide compounds generally suitable as catalyst components for purposes of the invention include the lanthanum, cerium, neodymium, praseodymium and didymium alkoxides (wherein R is $C_1$ to $C_{30}$ alkyl), including the lower alkoxides, e.g., lanthanum pentoxide, cerium isopropoxide, and didymium t-butoxide, as well as the higher alkoxides having one or more of their alkyl R substituents in the same $C_8$ to $C_{20}$ range as the most preferred alkanol reactant of the process, e.g., nonyl, decyl, dodecyl, and hexadecyl groups. Specific examples of preferred phenoxide compounds useful in this service include lanthanum phenoxide, lower alkyl-substituted phenol derivatives such as cerium benzyloxide and higher alkyl-substituted phenol derivatives, e.g., compounds wherein R represents nonylphenyl, tridecylphenyl, pentadecylphenyl, etc.

When the process is applied to alkoxylation of an alkanol reactant, particular preference exists for the use of alkoxide catalyst compound(s) in which each of the one or more "X" substituents which represents an —OR group is characterized by an alkyl group R which has a carbon number in the range from 1 to about 30, more preferably a carbon number in the range from about 1 to 20, and most preferably a carbon number which corresponds closely to the carbon number(s) of the particular alkanol reactant employed in a given process application. Thus, for instance, the reaction of a dodecyl alcohol reactant is most preferably conducted in the presence of a catalytic alkoxide compound for which the —OR substituents present have dodecyl alkyl groups R.

Without intention that the invention be limited to one theory or mechanism of operation, it is thought that soluble, basic compounds of the lanthanum series elements may undergo reaction with the active hydrogen containing reactant (and possibly also the alkoxylate product) to produce corresponding derivatives of the reactant (and of the alkoxylate product) which are the predominant active catalyst species in the typical alkoxylation reaction. Thus, for example, when the soluble, basic compound lanthanum n-butoxide is contacted with a higher alkanol alkoxylation reactant (e.g., a $C_{12}$ alkanol), a transalcoholysis reaction is believed to occur which liberates butanol and converts at least a portion of the lanthanum butoxide to lanthanum alkoxides having $C_{12}$ alkyl substituents. In this respect, the invention specifically encompasses lanthanum series compounds of a formula such as shown above wherein the X substituents which are —OR (or —SR, —NR, etc.) groups correspond to the reactant (absent the active hydrogen atom). Equivalently, the X substituents in such a formula may suitably correspond to alkoxylate molecules as are produced in the alkoxylation process (again absent an active hydrogen atom), for example, corresponding ethoxylates of the formulas $-(OCH_2CH_2)_n-OR$; $-(OCH_2CH_2)_n-SR$; and $-(OCH_2CH_2)_n-NR$. Lanthanum series compounds having such alkoxylate substituents are preferred for use in the invention, for reason of both solubility and catalytic effect.

It should be understood that the requirement for catalyst solubility means that not all catalyst compounds which may be suitable in one process embodiment are necessarily suitable in another. Thus, for instance, higher carbon number alkoxide compounds are more readily soluble in higher carbon number alkanol reactants than are the lower carbon number alkoxides. As a specific example, lanthanum n-butoxide is soluble in $C_{12}$ alkanol and effective for promoting alkoxylation, whereas lanthanum isopropoxide is insoluble in this same reactant and fails to catalyze its alkoxylation. In this respect, characteristics of particular lanthanum series compounds which favor solubility in active hydrogen containing reactants will be apparent to those skilled in the art.

The soluble basic lanthanum series compounds are present in the reaction mixture in a catalytically effective amount. Although a specific quantity of catalyst is not critical to the invention, preference may be expressed for use of the catalyst in amount of at least about 0.1% m, while an amount between about 0.2 and 5% m is considered more preferred and an amount between about 0.5 and 2% m is considered most preferred for typical embodiments. These percentages are in terms of the amount of catalyst relative to active hydrogen containing compounds in the reactant. Substantially greater quantities of catalyst, e.g., up to about 10% m or more, are also very suitable. As a rule, the higher the desired average alkylene oxide adduct number of the alkoxylate product and the higher the desired rate of reaction, the greater the required quantity of catalyst.

In terms of processing procedures, the alkoxylation reaction in the invention may be conducted in a generally conventional manner. For example, the catalyst may initially be mixed with liquid active hydrogen reactant. A substantially liquid mixture forms, although it is not necessary that all of the added catalyst dissolve in the reactant. This mixture is then contacted, preferably under agitation, with alkylene oxide reactant, which is typically introduced in gaseous form. The order in which the reactants and catalyst are contacted has not been found to be critical to the invention.

While these procedures describe a batch mode of operation, the invention is equally applicable to a continuous process.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30.

In general terms, suitable and preferred process temperatures and pressures for purposes of this invention are the same as in conventional alkoxylation reactions between the same reactants, employing conventional catalysts. A temperature of at least about 90° C., particularly at least about 130° C. and most particularly at least about 150° C., is typically preferred for a significant rate of reaction, while a temperature less than about 250° C., particularly less than about 210° C., and most particularly less than about 190° C., is typically desirable to minimize degradation of the product. As is known in the art, the process temperature can be optimized for given reactants, taking these factors into account.

Superatmospheric pressures, e.g., pressures between about 10 and 150 psig, are preferred, with pressure being sufficient to maintain the active hydrogen reactant substantially in the liquid state.

The active hydrogen reactant is a liquid and the alkylene oxide reactant is generally a vapor for such reactions. Alkoxylation is then suitably conducted by introducing gaseous alkylene oxide into a pressure reactor containing the liquid active hydrogen reactant and the catalyst. For considerations of process safety, the partial pressure of the lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours. In some instances the process is characterized by an induction period after the reactants and catalyst are contacted and before the alkoxylation reaction commences at a meaningful rate.

After the ethoxylation reaction has been completed, the product is preferably cooled and then neutralized to deactivate the catalyst. Neutralization is suitably accomplished by the addition of a acid (e.g., acetic acid, propionic acid, sulfuric acid, hydrochloric acid, etc.) to the basic product mixture. Neutralized catalyst residues are very suitably left in the product, or may be removed if desired, for example, by precipitation or extraction or the like.

The alkoxylate prepared in the process of the invention is typically a product of very acceptable quality, having a relatively low content of polyalkylene glycols and other by-products.

The following Examples are provided to further illustrate certain specific aspects of the invention but are not intended to limit its broader scope.

EXAMPLE 1

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched) alkanols having twelve and thirteen carbon atoms (about 40% by mole $C_{12}$ and 60% by mole $C_{13}$). Lanthanum n-butoxide—La(O-nBu)$_3$—was used as catalyst (or catalyst precursor). The catalyst was prepared by reaction of n-butanol with lanthanum methoxide which, in turn had been prepared by reaction of lithium methoxide with lanthanum chloride methanolate. Initially, 1.54 grams (0.0043 mols) of the lanthanum n-butoxide was added to 200 grams (1.03 mols) of the NEODOL 23. The resulting slurry was nitrogen sparged for one hour at 130° C. and then transferred to a one liter autoclave reactor maintained under nitrogen atmosphere. Temperature of the reactor and its contents was raised to 170° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 170° C. The process was characterized by a slow, steady uptake of ethylene oxide. After a total reaction time of 6 hours, ethylene oxide addition was discontinued. The reactor was maintained at 170° C. for an additional one hour to consume unreacted ethylene oxide in the system. The product mixture was then cooled and neutralized with acetic acid.

The product was analyzed by GC-LC techniques and found to have a mean average adduct number of 0.72. The ethylene oxide adduct distribution of the product is presented in Table I below. The distribution is more peaked than that characteristic of conventional products of alkali metal catalyzed ethoxylation. The product of this example also has a relatively low content of residual unreacted alcohol for an alkanol ethoxylate of this adduct number.

The only observed by-products were polyethylene glycols (PEG) in a quantity of about 1 percent by weight.

TABLE I

| Ethoxylate Distribution | |
|---|---|
| Adduct Number | Concentration |
| 0 (Residual Alcohol) | 49.96% w |
| 1 | 23.64 |
| 2 | 15.21 |
| 3 | 6.94 |
| 4 | 2.73 |
| 5 | 1.02 |
| 6 | 0.50 |

EXAMPLE 2

In another alkoxylation process embodiment according to the invention, 1.0 grams (0.003 mols) of tricyclopentadienyl lanthanum was added to 72 grams (0.371 mols) of NEODOL 23. The resulting mixture was nitrogen sparged for one hour at 130° C. A clear solution resulted which was then transferred under nitrogen atmosphere to the one liter autoclave reactor. Temperature of the reactor and its contents was raised to 170° C. A mixture of nitrogen and ethylene oxide was then introduced into the reactor to a total pressure of 75 psia (45 psia nitrogen and 30 psia ethylene oxide). Alkoxylation proceeded at a significant rate after an induction period of about 15 minutes. Additional ethylene oxide was supplied on demand. Temperature was maintained at 170° C. After a total reaction time of 3 hours, ethylene oxide addition was discontinued. The reactor was maintained at 170° C. for an additional one hour to consume unreacted ethylene oxide in the system. The product mixture cooled and neutralized with acetic acid.

The product was analyzed and found to have a mean average adduct number of 2.9. The ethylene oxide adduct distribution of the product is presented in Table II below. This distribution is more peaked and has a lower content of residual alcohol, relative to conventional alkali metal catalyzed ethoxylation products of like average adduct number.

The only observed by-product was PEG in a quantity of about 1 percent by weight.

TABLE II

| Ethoxylate Distribution | |
|---|---|
| Adduct Number | Concentration |
| 0 (Residual Alcohol) | 11.9% w |
| 1 | 7.8 |
| 2 | 11.9 |
| 3 | 16.6 |
| 4 | 17.7 |
| 5 | 14.3 |
| 6 | 9.7 |
| 7 | 5.4 |
| 8 | 2.6 |
| 9 | 1.1 |
| 10 | 0.5 |
| 11 | 0.2 |
| 12 | 0.1 |
| 13 | 0.1 |

I claim:

1. A process for the preparation of alkylene oxide adducts of active hydrogen containing organic compounds, which comprises contacting and reacting reactants consisting of (a) an alkylene oxide reactant selected from the group consisting of ethylene oxide, propylene oxide and mixtures thereof and (b) one or more active hydrogen containing organic compounds, in the presence of a catalytically effective amount of one or more soluble basic compounds of one or more of the elements of the lanthanum series, with the provision that said soluble basic compounds are sufficiently basic that a one percent by weight mixture of the compounds in water has a pH greater than 8.0.

2. The process of claim 1, wherein the active hydrogen containing reactant consists essentially of one or more active hydrogen containing compounds selected from the group consisting of alcohols, phenols and polyols.

3. The process of claim 2, wherein the active hydrogen containing reactant consists essentially of one or more active hydrogen containing compounds selected from the group consisting of alcohols having from one to about 30 carbon atoms and alkyl-substituted phenols wherein each alkyl substituent has from one to about 30 carbon atoms.

4. The process of claim 2, wherein the active hydrogen containing reactant consists essentially of one or more alkanols.

5. The process of claim 4, wherein the active hydrogen containing reactant consists essentially of primary mono-hydric alkanols having carbon numbers in the range from 6 to 24, inclusive.

6. The process of claim 5, wherein the active hydrogen containing reactant consists essentially of primary mono-hydric alkanols having carbon numbers in the range from 8 to 20, inclusive.

7. The process of claim 6, wherein greater than about 50% of the molecules of the primary mono-hydric alkanols are of linear carbon structure.

8. The process of claim 7, wherein greater than about 70% of the molecules are of linear carbon structure.

9. A process for the preparation of ethylene oxide adducts of alkanols, which comprises contacting and reacting reactants consisting of (a) ethylene oxide and (b) one or more alkanols in the presence of a catalytically effective amount of one or more soluble basic compounds of one or more of the elements of the lanthanum series, with the provision that said soluble basic compounds are sufficiently basic that a one percent by weight mixture of the compounds in water has a pH greater than 8.0.

10. The process of claim 9, wherein the alkanols are monohydric $C_6$ to $C_{24}$ alkanols.

11. The process of claim 10, wherein the alkanols are primary alkanols.

12. The process of claim 11, wherein greater than about 50% of the alkanol molecules are of linear carbon structure.

13. The process of claim 12, carried out in the presence of a catalytically effective amount of one or more soluble basic compounds of one or more elements selected from the group consisting of lanthanum, cerium, neodymium, and praseodymium.

14. The process of claim 9, carried out in the presence of a catalytically effective amount of one or more compounds selected from the alcoholates and phenolates of one or more of the elements of the lanthanum series.

15. The process of claim 13, carried out in the presence of a catalytically effective amount of one or more compounds selected from alcoholate and phenolate compounds.

16. The process of claim 15, carried out in the presence of one or more alkoxide compounds.

17. The process of claim 16, wherein the alkoxide compounds have —OR substituents wherein R is an alkyl group in the $C_8$ to $C_{20}$ range.

18. The process of claim 17, wherein the alkoxide compounds have at least one —OR substituent corresponding to the alkanols in the active hydrogen containing reactant.

19. A process for the preparation of ethylene oxide adducts of alkanols, which comprises contacting and reacting reactants consisting of (a) ethylene oxide and (b) one or more $C_8$ to $C_{20}$ alkanols in the presence of a catalytically effective amount of one or more soluble basic compounds of one or more of the elements of the lanthanum series, with the provision that said soluble basic compounds are sufficiently basic that a one percent by weight mixture of the compounds in water has a pH greater than 8.0.

20. The process of claim 19, carried out in the presence of a catalytically effective amount of one or more soluble basic compounds of one or more members of the group consisting of lanthanum, cerium, neodymium, and praseodymium.

21. The process of claim 20, carried out in the presence of a catalytically effective amount of one or more soluble basic compounds of lanthanum.

22. The process of claim 21, carried out in the presence of a catalytically effective amount of one or more soluble basic alkoxides of lanthanum.

23. The process of claim 20, carried out in the presence of a catalytically effective amount of one or more soluble basic compounds of cerium.

24. The process of claim 23, carried out in the presence of a catalytically effective amount of one or more soluble basic alkoxides of cerium.

25. The process of claim 20, carried out in the presence of a catalytically effective amount of soluble basic compounds of didymium.

26. The process of claim 25, carried out in the presence of a catalytically effective amount of soluble basic alkoxides of didymium.

27. A process for the preparation of alkylene oxide adducts of active hydrogen containing organic compounds, which comprises contacting and reacting an alkylene oxide reactant selected from the group consisting of ethylene oxide, propylene oxide and mixtures thereof with one or more active hydrogen containing organic compounds, in the presence of a catalytically effective amount of one or more soluble basic compounds of one or more elements of the lanthanum series selected from the group consisting of lanthanum, neodymium and praseodymium, with the provision that said soluble basic compounds are sufficiently basic that a one percent by weight mixture of the compounds in water has a pH greater than 8.0.

28. The process of claim 27, wherein the active hydrogen containing reactant consists essentially of one or more active hydrogen containing compounds selected from the group consisting of alcohols, phenols and polyols.

29. The process of claim 28, wherein the alkylene oxide reactant consists essentially of ethylene oxide.

30. The process of claim 29, wherein the active hydrogen containing reactant consists essentially of primary mono-hydric alkanols having carbon numbers in the range from 6 to 24, inclusive.

* * * * *